United States Patent
Sonnleitner

(10) Patent No.: US 10,624,747 B2
(45) Date of Patent: Apr. 21, 2020

(54) METHOD FOR PRODUCING A MULTILAYER FILM

(71) Applicant: Dietmar Sonnleitner, Salzburg (AT)

(72) Inventor: Dietmar Sonnleitner, Salzburg (AT)

(*) Notice: Subject to any disclaimer, the term of this patent is extended or adjusted under 35 U.S.C. 154(b) by 328 days.

(21) Appl. No.: 15/423,969

(22) Filed: Feb. 3, 2017

(65) Prior Publication Data
US 2017/0143492 A1   May 25, 2017

Related U.S. Application Data

(63) Continuation of application No. PCT/AT2015/000098, filed on Jul. 15, 2015.

(30) Foreign Application Priority Data

Aug. 5, 2014 (AT) .................................. A 622/2014

(51) Int. Cl.
*A61F 2/28* (2006.01)
*A61C 19/00* (2006.01)
*A61F 2/30* (2006.01)

(52) U.S. Cl.
CPC .......... *A61F 2/2846* (2013.01); *A61C 19/00* (2013.01); *A61F 2002/30014* (2013.01);
(Continued)

(58) Field of Classification Search
CPC .............. A61F 2/0063; A61F 2/2846; A61F 2310/00359; A61F 2/2875;
(Continued)

(56) References Cited

U.S. PATENT DOCUMENTS 4,817,594 A * 4/1989 Juhasz ............... A61L 15/18
204/415
5,380,328 A   1/1995 Morgan
(Continued)

FOREIGN PATENT DOCUMENTS

CN          1187116       7/1998
CN        101400381       4/2009
(Continued)

OTHER PUBLICATIONS

Ghanaati et al. "Evaluation of the Tissue Reaction to a New Bilayered Collagen Matrix in Vivo and it translation to the clinic" Biomedical Materials 6 (2011). (Year: 2011).*
(Continued)

*Primary Examiner* — Brian A Dukert
*Assistant Examiner* — Rebecca Lynee Zimmerman
(74) *Attorney, Agent, or Firm* — Wenderoth, Lind & Ponack, L.L.P.

(57) ABSTRACT

A method produces a multilayer film for covering a bone defect site. The film comprises at least one substantially completely bioresorbable covering layer, and the at least one covering layer is placed on a thermally deformable and substantially completely bioresorbable molding layer. The at least one covering layer is connected to the molding layer thermally and/or mechanically, preferably in a compressed manner. Mandrel-like protrusions are arranged on the molding layer, and the protrusions are pressed into the at least one covering layer by the placement of the at least one covering layer on the molding layer and/or pushed through the at least one covering layer. Alternatively or in addition to the protrusions, substantially completely bioresorbable connection devices, preferably rivets or pins, are pushed through the molding layer and the at least one covering layer.

33 Claims, 11 Drawing Sheets

(52) U.S. Cl.
CPC ............... *A61F 2002/30062* (2013.01); *A61F 2002/30065* (2013.01); *A61F 2002/3092* (2013.01); *A61F 2002/30433* (2013.01); *A61F 2002/30451* (2013.01); *A61F 2002/30477* (2013.01); *A61F 2002/30578* (2013.01); *A61F 2002/30971* (2013.01); *A61F 2002/30973* (2013.01)

(58) Field of Classification Search
CPC . A61F 2002/30971; A61F 2002/30973; A61B 17/80; A61B 2090/3991; A61B 5/0088; A61L 2430/34; B32B 7/08; B32B 3/30; B32B 37/144; B01J 31/124; A61C 19/00
USPC ...................................................... 623/23.51
See application file for complete search history.

(56) References Cited

U.S. PATENT DOCUMENTS

| | | | |
|---|---|---|---|
| 5,443,483 | A | 8/1995 | Kirsch |
| 6,031,148 | A | 2/2000 | Hayes et al. |
| 6,143,293 | A * | 11/2000 | Weiss ..................... A61L 27/18 424/423 |
| 6,350,284 | B1 | 2/2002 | Törmälä |
| 8,524,265 | B2 | 9/2013 | McKay |
| 9,962,250 | B2 * | 5/2018 | Priewe ................... A61F 2/0063 |
| 2006/0224242 | A1 * | 10/2006 | Swords ................ A61B 17/8085 623/17.19 |
| 2008/0044449 | A1 | 2/2008 | McKay |
| 2009/0157194 | A1 | 6/2009 | Shikinami |
| 2010/0119564 | A1 | 5/2010 | Kasuga et al. |
| 2013/0288199 | A1 | 10/2013 | Wen |
| 2015/0057762 | A1 * | 2/2015 | Harms ................... A61L 31/148 623/23.74 |
| 2015/0099093 | A1 * | 4/2015 | Arbesman ................ B32B 3/30 428/139 |
| 2015/0265407 | A1 | 9/2015 | Horvath |
| 2015/0374497 | A1 * | 12/2015 | Engstrand ............. A61F 2/2846 623/17.19 |

FOREIGN PATENT DOCUMENTS

| | | | |
|---|---|---|---|
| DE | 43 13 192 | 9/1994 | |
| DE | 196 54 884 | 9/1997 | |
| JP | 2002-325830 | 11/2002 | |
| JP | 2005-230211 | 9/2005 | |
| WO | 92/10218 | 6/1992 | |
| WO | 00/15152 | 3/2000 | |
| WO | 2008/021921 | 2/2008 | |
| WO | WO-2011119845 A1 * | 9/2011 | ........... A61F 2/0063 |
| WO | 2012/075004 | 6/2012 | |
| WO | 2014/086913 | 6/2014 | |

OTHER PUBLICATIONS

Makadia et al "Poly Lactic-co-Glycolic Acid (PLGA) as Biodegradable Controlled Drug Delivery Carrier" Polymers (2011) 3(3): 1377-1397. (Year: 2011).* http://www.mdpsupplies.ie/datasheets/mdpsecaboheatpresses.pdf (Year: 2011).*

English Translation of Search Report dated Dec. 15, 2017 in Chinese Application No. 201580042099.4.

International Search Report dated Nov. 4, 2015 in International (PCT) Application No. PCT/AT2015/000098.

Search Report dated Jan. 28, 2015 in Austrian Application No. A 622/2014, with English translation.

* cited by examiner

METHOD FOR PRODUCING A MULTILAYER FILM

BACKGROUND OF THE INVENTION

The invention concerns a method of producing a multilayer film and a multilayer film for covering a bone defect site.

Known films or membranes for covering bone defect sites are used, for example, in the field of jawbone or jaw augmentation in order to reconstruct a jawbone in the case of bone shrinkage or bone loss which can occur upon the extraction of a tooth or as a consequence of an inflammatory process around a natural tooth or an implant. Such films frequently have a shape structure of titanium which is arranged on a Teflon membrane and which is shaped over the bone defect site so that formed between the film and the bone defect site is a cavity in which bone material and in the case of natural teeth also the periodontium can subsequently grow. Fixing of the film is usually effected with bioresorbable or metal pins or screws which are fixed through the film to the jawbone. Alternatively, the film can also be glued to the base or to the jawbone. With implants which are introduced at the same time, the film can also be fixed to the implant head. As bone regeneration requires a number of months, a second operation is required after bone construction has occurred with a Teflon membrane in order to remove the film or Teflon membrane from the body again.

Cover layers of bioresorbable materials are also already known, which are dissolved by the body again by virtue of their bioresorbability, for example by hydrolysis. Such cover layers, however, generally suffer from excessively low stability in respect of shape in order to permit and maintain a structure for promoting bone healing during the duration of bone healing. The use of such a cover layer in conjunction with a shaping Teflon membrane again requires a second operation to remove the Teflon membrane from the body again.

The object of the invention is to avoid the above-described disadvantages and to provide a method which is improved over the state of the art of producing a multilayer film, as well as a multilayer film which is improved over the state of the art. In particular, the invention seeks to avoid a further operation for removal of the film.

SUMMARY OF THE INVENTION

To achieve the above object, a cover layer is applied to a thermally deformable and substantially completely bioresorbable molding layer. The cover layer is thermally and/or mechanically connected to the molding layer, preferably being pressed thereto, and connected by connecting elements.

The term thermal connection is used inter alia to mean that the molding layer and/or the at least one cover layer is or are heated by applying heat from an external heat source (for example, a heated pressing device) above the respective melting point, whereby the molding layer and the cover layer fuse together by, for example, the molding layer penetrating into or surrounding the cover layer. The molding layer and the cover layer are thus connected together and a firm connection is made after hardening of the fused molding layer and/or cover layer.

The term mechanical connection is used to mean, inter alia, positively locking or force-locking connections (i.e., connecting elements) which can be suitable connecting devices such as rivets or pins. In that case, connecting devices can be arranged, preferably formed in one piece, on the molding layer and/or the at least one cover layer. The connecting elements, however, can also involve separate connecting members with which the molding layer and the cover layer are connected together, for example, by being pressed together in a pressing device.

A proposed film therefore includes at least one cover layer and a shaping molding layer, wherein both the cover layer and also the shaping molding layer are bioresorbable in the body.

The at least one cover layer which can be, for example, in the form of a membrane can serve to cover over and seal off a bone defect site to avoid the ingress of soft tissue into the bone defect site (i.e., the cover layer and film are non-mesh). It can also be flexible and preferably elastic to permit good coverage and sealing of the bone defect site. To further improve application of the film and sealing of the bone defect site, the cover layer can also be such that it adheres to a gum surrounding the bone defect site.

The shaping molding layer can be in the form of a layer which is substantially stable in shape and which can be deformed both under thermal and also mechanical and/or chemical influence, and which after such deformation is again of sufficient stability in shape to maintain the cavity to be formed for bone growth for the required period of time. The molding layer can serve, in particular, for adaptively shaping the film to a bone defect site.

A cavity can be formed between the bone defect site and the film by the shaping molding layer so that bone growth can take place in that cavity. For advantageous bone regeneration, the cavity can also contain bone substitute materials and/or carriers for drugs, growth factors and/or other substances which promote and protect healing and bone formation. The cavity can be maintained by the cavity-forming and cavity-retaining molding layer until the cavity is filled up by further growth of bone material.

The proposed method permits the production of a pre-bonded multilayer film including a shaping molding layer and at least one cover layer.

The fact that both the at least one cover layer and also the molding layer are bioresorbable means that the film or membrane can be overall completely broken down in the body (for example by hydrolysis). Thus, there is no need to perform a further operation for removal of the film. In other words, in this case only one operation is required for fitting the film.

The fact that the at least one cover layer with the shaping molding layer is provided in the form of a multilayer film which is already pre-bonded affords an easily handlable film for covering a bone defect site. This pre-bonded multilayer film links the space-forming properties of the molding layer to the sealing properties of the cover layer, and is substantially completely resorbed in the body.

The multilayer film produced by the method according to the invention can in this case be widely used as a surgical and/or therapeutic film. Thus, besides the specific application in the field of jaw augmentation, a proposed multilayer film can also be used in orbital cavity fractures, fractures of the skull, and generally in the field of neurosurgery and traumatology and generally for surgical and/or therapeutic purposes.

In a preferred embodiment of the invention, at least the molding layer is heated for thermally connecting the at least one cover layer to the molding layer. Preferably in that case, the molding layer can be heated to a temperature in the region of between about 50° C. and about 70° C., preferably to a temperature of about 60° C. Because the molding layer is thermally deformable it can be thermally connected to the at least one cover layer by the action of heat from the exterior, by the molding layer being fused for example to the cover layer.

Spike-like projections can be arranged on the molding layer as connecting elements, and the projections are pressed into the at least one cover layer and/or are pushed through the at least one cover layer by application of the at least one cover layer to the molding layer.

Alternatively or additionally, prior to the thermal and/or mechanical connection being made, the connecting elements can be substantially completely bioresorbable connecting devices, preferably rivets or pins, fitted through the molding layer and the at least one cover layer. Preferably, the connecting devices are also thermally deformable. Here too, when the molding layer is pressed to the at least one cover layer—preferably under the action of heat from the exterior—the ends of the connecting devices are deformed in a rivet shape and thus produce an improved connection between the layers, for example in the form of a rivet connection.

Preferably, the projections are shaped in one piece on the molding layer. The provision of projections on the molding layer makes it possible to achieve an improved mechanical connection between the molding layer and the at least one cover layer. If the molding layer and also the projections thereof are thermally deformable, then the projections can be thermally connected to the at least one cover layer by an action of heat from the exterior, by the projections being fused for example in the cover layer. If the projections protrude through the at least one cover layer, then the ends of the projections can be deformed for example in a mushroom head-like configuration upon producing the mechanical and/or thermal connection between the molding layer and the at least one cover layer, and thus provide an improved connection between the layers.

In a preferred embodiment, the ends of the spike-like projections can be in the form of barbs or mushroom heads. That strengthens the connection between the molding layer and the at least one cover layer as the barbs or mushroom heads of the spike-like projections can hookingly engage in the at least one cover layer in the manner of a hook-and-loop fastener.

In a further variant, a first cover layer, a second cover layer, and a molding layer are arranged sandwich-like, the molding layer being disposed between the first cover layer and the second cover layer. In that respect, the molding layer has a smaller surface area than the first cover layer and the second cover layer. Preferably, the first cover layer is connected, preferably interlaced, directly with the second cover layer. Thus, the first cover layer and the second cover layer can be interlaced at their outer edges, in which case the molding layer is arranged within the outer edges of the first cover layer and the second cover layer between the first cover layer and the second cover layer.

Preferably, the at least one cover layer is pressed to the molding layer in a pressing apparatus. In that case, during the pressing operation, at least one surface of the pressing apparatus, that is facing towards the film, is heated, preferably to a temperature in the region of between about 50° C. and about 70° C., particularly preferably to a temperature of about 60° C.

The at least one cover layer can be thermally and/or mechanically connected to a thermally deformable and substantially completely bioresorbable molding layer.

Arranged on the molding layer can be connecting elements in the form of spike-like projections, wherein the projections are preferably formed in one piece on the molding layer.

Alternatively or additionally, the connecting elements can be substantially completely bioresorbable connecting devices, preferably rivet or pins, are fitted through the molding layer and the at least one cover layer.

In a preferred embodiment, the molding layer and the at least one cover layer are substantially completely bioresorbable in different periods of time. Thus, for example, by virtue of the nature of the molding layer and the at least one cover layer, it is possible that the molding layer resorbs more quickly than the at least one cover layer. In general, differing degrees of resorption capability in respect of the molding layer and the at least one cover layer afford great degrees of freedom in terms of the design of the film in relation to its resorption capability.

The film can be substantially completely resorbable overall in a period of time of between about 3 and 12 months, preferably between about 4 and 6 months. That is the period of time within which bone reconstruction has occurred in a normal situation.

To permit good adaptive molding to the bone defect site and stable cavity formation between the film and the bone defect site, the molding layer can be stiffer than the at least one cover layer. In that case, the greater stiffness of the molding layer serves to form a cavity for bone construction and also to maintain that cavity for the period of time required for bone regeneration. Once again, good coverage and sealing of the bone defect site can be achieved by the at least one cover layer being of lesser stiffness in comparison with the molding layer.

Preferably, the molding layer, possibly together with the at least one cover layer, is adapted to be both thermally and also mechanically and/or chemically deformable. Thus, particularly the molding layer can be in the form of a layer which is substantially stable in respect of shape, and which can be deformed both under thermal and also under mechanical or chemical influence, and after that deformation again has adequate stability in respect of shape to maintain the cavity to be formed for bone growth for the required period of time. The at least one cover layer can be flexible and preferably elastic to permit good coverage and sealing of the bone defect site.

Mechanical deformation can be effected in that case for example by bending with a forceps. This is a suitable method of shaping molding in particular for comparatively thin molding layers (for example, in the region of between about 0.10 mm and about 0.5 mm). For thicker molding layers (for example thicker than about 0.5 mm) thermal deformation of a molding layer for adaptive molding may be desirable. A corresponding thermal deformation procedure can be achieved in that case for example by a thermal bar having a hot tip or surface, by way of heated prefabricated models or in a hot water bath with a sterile saline solution.

For good bioresorption capability of the proposed film, the at least one cover layer at least partially and preferably substantially completely comprises a bioresorbable collagen material. In that case, the bioresorbable collagen material includes type-I-collagen and/or type-III-collagen. The collagen material can originate, for example, from bovine Achilles tendons.

In addition, the at least one cover layer at least partially comprises poly(lactic-co-glycolic acid)-polyethylene glycol-poly(lactic-co-glycolic acid). That material is commercially available for example by the name "vicryl mesh".

The at least one cover layer can be in the form of a membrane which at least partially comprises fibrin.

Further, the at least one cover layer can be in the form of a lyophilized membrane which at least partially comprises bovine pericardium or bovine dura mater.

For good bioresorbability of the proposed film, the molding layer can at least partially and preferably substantially completely comprise a bioresorbable polymer material. The bioresorbable polymer material can also be a co-polymer material.

A particular variant provides that the bioresorbable polymer material includes lactic acid, preferably L-lactic acid and/or derivates thereof. In that respect, it is advantageous if the proportion of lactic acid in the bioresorbable polymer material is at least 70%, preferably between about 80% and 95%, particularly preferably substantially about 82%.

Furthermore, the bioresorbable polymer material can include glycolic acid. It is advantageous in that case if the proportion of glycolic acid in the bioresorbable polymer material is at most 30%, preferably between about 15% and 20%, particularly preferably substantially about 18%. Depending on the respective composition of the molding layer, the molding layer is substantially stable in shape and nonetheless substantially completely bioresorbable.

The molding layer can at least partially comprise a polyester from the family of poly-α-hydroxyl acids like polytrimethylene carbonate, polydioxanone, polyglycolide, polylactide, poly(L-lactide-co-glycolide), besides other copolymers, polyorthoesters and/or polycaprolactone (polyhydroxybutyrate and polyhydroxybutrate-co-hydroxyvalerate).

The molding layer can at least partially comprise poly(D,L-lactide).

The molding layer can at least partially comprise poly(L-lactide-co-D,L-lactide).

In a further preferred embodiment, the molding layer and the at least one cover layer can have different surface areas. In that respect, the molding layer involves a smaller surface area than the at least one cover layer. If the at least one cover layer covers over the molding layer by virtue of its smaller area, it is possible to achieve particularly good coverage and thus also sealing of the bone defect site.

Preferably, the cover layer and/or the molding layer is or are substantially laminar (flat or planar) throughout. A film contour which is advantageous for adaptive shaping to the bone defect site can be achieved in that case, for example, by suitably cutting the film.

It is particularly desirable, however, if the molding layer has a shaping structure for adaptive molding to the bone defect site. In that respect, the shaping structure has at least portion-wise a convexly and/or concavely curved edge and/or at least portion-wise a convexly and/or concavely curved shape. In other words, the shaping structure can have, for example, areal—convexly and/or concavely curved—projections and can thus have a convexly and/or concavely curved edge. Alternatively or additionally, the shaping structure as a whole can also have a correspondingly convexly and/or concavely curved shape.

It is particularly advantageous if the shaping structure has at least one strut-shaped shaping molding element. The strut-shaped or lug-shaped shaping molding element can in that case be shaped loop-like over the bone defect site and can permit any cavity shape.

A particularly advantageous embodiment of the invention is that in which the shaping structure is substantially grid-shaped. The grid-shaped structure in that case forms a reinforcing grid which permits the formation of a plurality of any desired cavity shapes.

The shaping structure can also be provided by at least one reinforcement of the molding layer. Particularly, if the molding layer is applied in the form of a hardening liquid or a hardening gel to the cover layer, it is desirable if the shaping structure can be achieved merely by applying more liquid or gel in the region of the shaping structure. In that case, for example, the molding layer can have differing thicknesses with the thicker area serving to reinforce the strength of the molding layer.

A particular variant provides that the film has a carrier layer for at least one substance which is or which is to be arranged thereon. The substances which are arranged or which are to be arranged on the carrier layer can involve drugs, growth factors, or other substances which promote and protect healing and bone formation. The carrier layer can preferably be arranged at the side of the film, that is to face towards the bone defect site, and can at least partially and preferably substantially completely comprise a bioresorbable collagen material.

Corresponding substances can also be applied directly to the molding layer and/or the at least one cover layer. The surface or side of the film, that is to face towards a bone defect site, itself serves as a carrier for the above-described substances, by for example that side or surface of the film having appropriate roughness.

Depending on the respective situation of use, the proposed film or membrane can also be provided in pre-cut and/or pre-shaped form. In that respect, for example, a desired form of cut and/or a desired 3D deformation of the film can be effected in accordance with a data processing-aided planning procedure.

BRIEF DESCRIPTION OF THE DRAWINGS

Further details and advantages of the present invention are described by the specific description hereinafter. In the drawings.

DETAILED DESCRIPTION OF THE INVENTION

Figure 1:
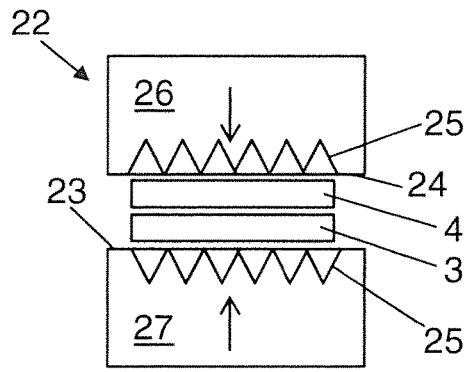
FIG. 1 diagrammatically shows a pressing apparatus for producing a proposed multilayer film.

FIG. 1 diagrammatically shows a side view of a pressing apparatus 22 for producing a proposed multilayer film 1. The pressing apparatus 22 has two pressing jaws 26, 27 with pressing surfaces 23, 24, between which are arranged a cover layer 4 and a molding layer 3. Both the cover layer 4 and also the molding layer 3 are bioresorbable. The molding layer 3 is also thermally deformable, that is to say the molding layer 3 can be deformed under the action of heat from the exterior.

The pressing apparatus 22 is equipped with at least one heating device 25 which makes it possible for the surfaces 23 and 24 of the pressing apparatus, that face towards the film 1, to be heated whereby consequently the film 1 or at least the thermally deformable molding layer 3 of the film 1 can be heated. By moving pressing jaws 26, 27 of the pressing apparatus 22 in the direction indicated by the arrow, the cover layer 4 applied to the molding layer 3 is thermally and/or mechanically connected to the molding layer 3, preferably by pressing. The surfaces 23, 24 of the pressing jaws 26, 27 of the pressing apparatus can be heated to the same temperature or also to different temperatures by the at least one heating device 25.

Figure 2:
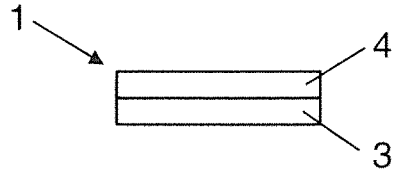
FIG. 2 is a diagrammatic side view of a multilayer film produced with the proposed method.

FIG. 2 shows the film of FIG. 1 after the connection is produced by the pressing apparatus 22. The cover layer 4 and the molding layer 3 are fixedly connected together and form a bonded multilayer film 1.

Figure 3A:
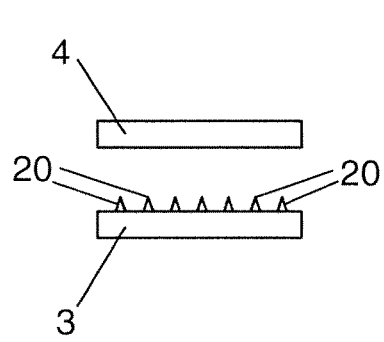
FIGS. 3a-3c show an embodiment of the production of a proposed multilayer film with a molding layer with spike-like projections formed thereon.
Figure 3B:
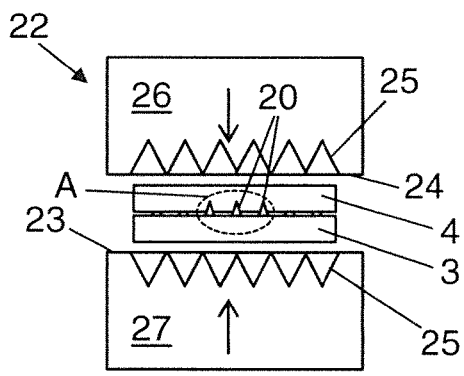
Figure 3C:
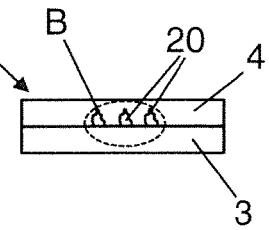

FIGS. 3a through 3c show the production of a further proposed multilayer film 1. FIG. 3a shows two layers of the film 1 to be produced, more specifically a cover layer 4 and a molding layer 3. The molding layer 3 has connecting elements in the form of spike-shaped projections 20 which in this example are formed in one piece on the molding layer 3. Upon or due to application of the cover layer 4 to the molding layer 3, the projections 20 bore into the cover layer 4, but in this example do not project through the cover layer 4. FIG. 3b shows the arrangement of the cover layer 4 and the molding layer 3 after application of the cover layer 4 to the molding layer 3. In a pressing apparatus 22 with heating device 25, the cover layer 4 is now mechanically and thermally connected to the molding layer 3 by the pressing jaws 26, 27 of the pressing apparatus 22 being moved towards each other in the direction of the arrow and in so doing pressing the cover layer 4 to the molding layer 3. During that pressing operation, the molding layer 3 can be heated, for example, to a temperature in the region of between about 50° C. and about 70° C., by heating of a surface 23 of the pressing jaw 27 and/or a surface 24 of the pressing jaw 26 by the heating device 25. By virtue of that action of heat from the exterior, the projections 20 can be melted whereby the projections 20 of the molding layer 3 can fuse with the cover layer 4, as shown in FIG. 3c. The regions A, B marked in FIGS. 3b and 3c respectively show a broken-away region of the film 1 in order to show how the projections 20 penetrate within the film 1 into the cover layer 4 and fuse to the cover layer 4. Besides fusing of the molding layer 3 to the cover layer 4, the projections 20 which are fused into the cover layer 4 permit a firm, dowel-like connection.

Figure 4A:
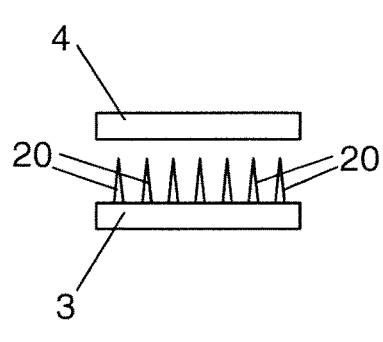
FIGS. 4a-4c show a further embodiment of the production of a proposed multilayer film with a molding layer with spike-like projections formed thereon.
Figure 4B:
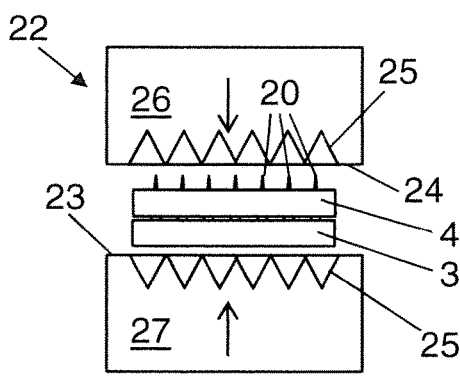
Figure 4C:
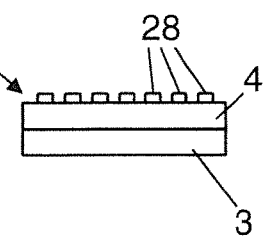

FIGS. 4a through 4c show a further example of a method of producing a proposed film 1. Similarly to FIG. 3a, here too the molding layer 3 has projections 20 which in this example however are so long that, when the cover layer 4 is applied to the molding layer 3, the projections protrude through the cover layer 4 as shown in FIG. 4b. By virtue of the cover layer 4 being pressed to the molding layer 3 by the pressing apparatus 22, the tips of the projections 20 which protrude through the cover layer 4 are deformed like a mushroom heads 28 so that a firmly bonded multilayer film 1 is produced, as shown in FIG. 4c. In addition to a connection in respect of the mutually contacting surfaces of the cover layer 4 and the molding layer 3, the heads 28 of the projections 20 that are formed by the thermal pressing operation provide for a positively locking connection between the cover layer 4 and the molding layer 3.

Figure 5A:
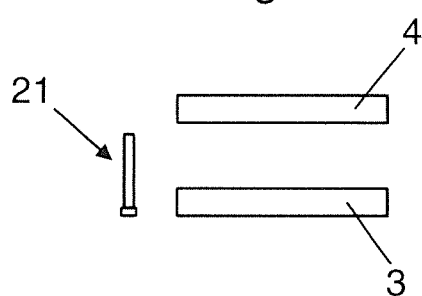
FIGS. 5a-5d show an embodiment of the production of a proposed multilayer film using rivet-like connecting devices.
Figure 5B:
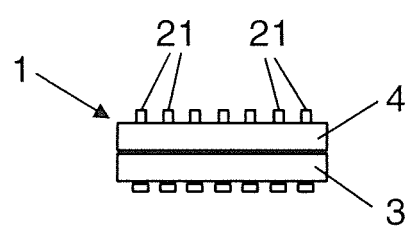
Figure 5C:
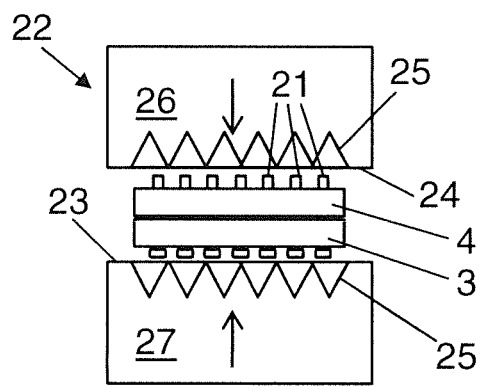
Figure 5D:
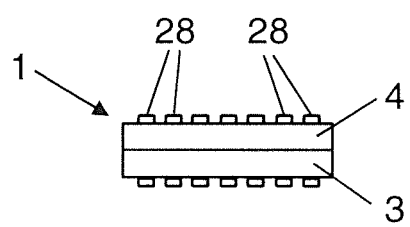

FIGS. 5a through 5d show a further example of the production of a proposed multilayer film 1. In this case, as shown in FIG. 5a, besides a cover layer 4 and a molding layer 3, connecting elements in the form of a plurality of connecting devices 21 such as rivets or pins are used. FIG. 5b shows the cover layer 4 applied to the molding layer 3 and a plurality of connecting devices 21 which are fitted through the molding layer 3 and the cover layer 4. In this example, the connecting devices 21 are provided with a head at one end, and the heads bear against the molding layer 3 and the free ends of the connecting devices 21 project through the molding layer 3 and the cover layer 4 and extend beyond the cover layer 4. As shown in FIG. 5c, the arrangement of FIG. 5b is introduced into a pressing apparatus 22 and thermally pressed by pressing jaws 26, 27 of the pressing apparatus 22. FIG. 5d shows the finished multilayer film 1. It can be seen in this case that the free ends of the connecting devices 21 were deformed by the pressing operation in such a way that heads 28 were formed, which bear against the cover layer 4. That gives a firm positively locking connection in the manner of a rivet connection.

Figure 6:
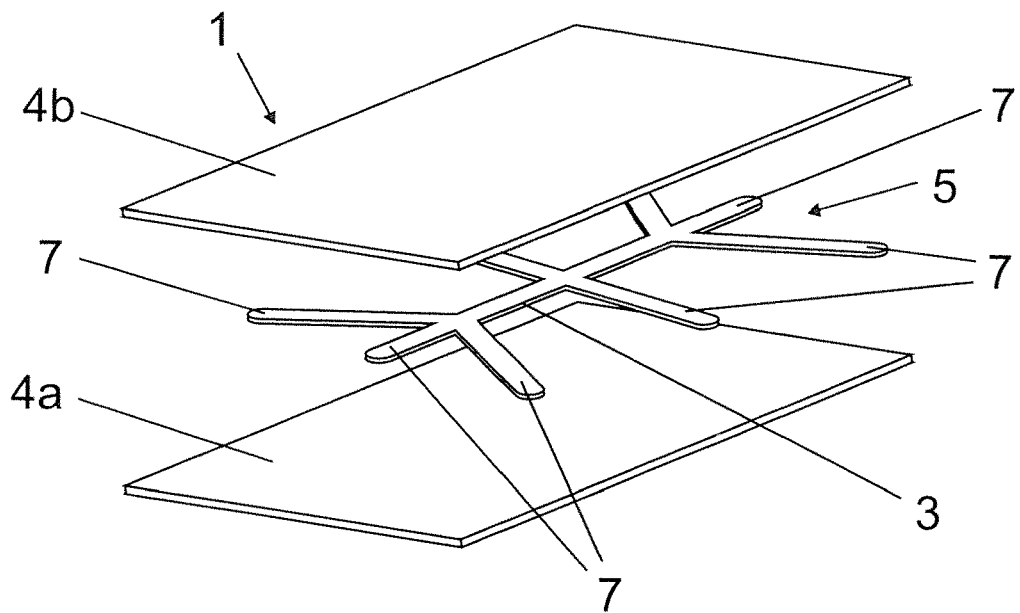
FIG. 6 is an exploded perspective view of an embodiment of the proposed multilayer film.

FIG. 6 shows an exploded perspective view of a proposed pre-bonded multilayer film 1. The film 1 includes a molding layer 3 and two cover layers 4a and 4b. The molding layer 3 is stiffer than the cover layers 4a and 4b and has a shaping structure 5. The shaping structure 5 includes a plurality of strut-shaped shaping molding elements 7 which serve to shape the film 1 over a bone defect site 2 (not shown here), in which case the film 1 can be well adaptively shaped to a bone 11, that is still present, of the bone defect site 2 (see for example FIG. 30) by the adaptive molding elements 7. The shaping structure 5 generally has a substantially grid-shaped configuration and thus permits the provision of any surface shapes for the film 1 so that, in conjunction with a bone defect site 2, any desired cavity shapes can be formed between the film 1 and the bone defect site 2. In the illustrated example, the shaping structure 5 has a longitudinally extended adaptive molding element 7 from which further adaptive molding elements 7 project branch-like. The shaping structure 5 can be very well adapted in shape to a bone 11 which is still present at the bone defect site 2 by the molding elements 7 projecting in branch-like form.

The molding layer 3 and the cover layers 4a and 4b respectively comprise a bioresorbable material so that the film overall can be substantially completely bioresorbed in the body. By virtue of the provision of two cover layers 4a and 4b, between which the molding layer 3 is embedded, it is possible to control in particular the resorption speed and mechanical strength of the molding layer.

The cover layers 4a and 4b can, for example, comprise bioresorbable collagen membranes which on the one hand by virtue of their softness can well cover a bone defect site 2 and which on the other hand can be well secured by adhesive to a gum 13 surrounding the bone defect site 2 so as to ensure that the bone defect site 2 is well sealed off.

The molding layer 3 can comprise, for example, a bioresorbable polymer material or co-polymer material. In particular, the molding layer 3 can include for example about 82% L-lactic acid and about 18% glycolic acid. Such a choice of material affords a molding layer 3 which is substantially stable in respect of shape and which can be adapted to be thermally and also mechanically and/or chemically deformable for adaptive molding to a bone defect site 2, wherein after such deformation the molding layer is again substantially stable in shape. By virtue of the stiffness and stability of shape of the molding layer 3, it is thus possible to provide a cavity for bone regeneration between the film 1 and the bone defect site 2, and also to maintain it for the period of bone regeneration.

Figure 7:
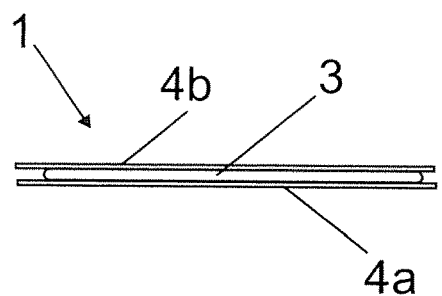
FIG. 7 is a side view of the proposed multilayer film of FIG. 6.

FIG. 7 shows a side view of the bonded multilayer film 1 of FIG. 6.

Figure 8:
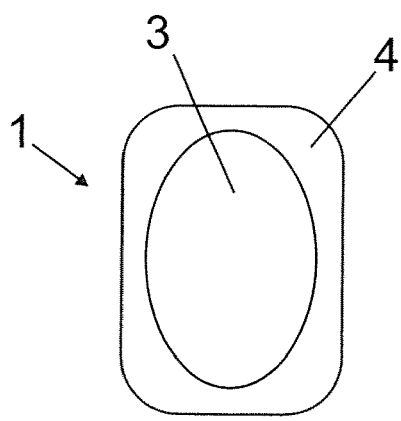
FIG. 8 is a plan view of a further embodiment of the proposed multilayer film.

FIG. 8 shows a plan view of a further variant of the proposed film 1 which in this example has a double-layer structure and includes a molding layer 3 and a cover layer 4. Both the molding layer 3 and the cover layer 4 are substantially flat. The film 1 can be cut to shape as desired to permit good adaptive shaping to a bone defect site 2 depending on the respective situation of use.

Figure 9:
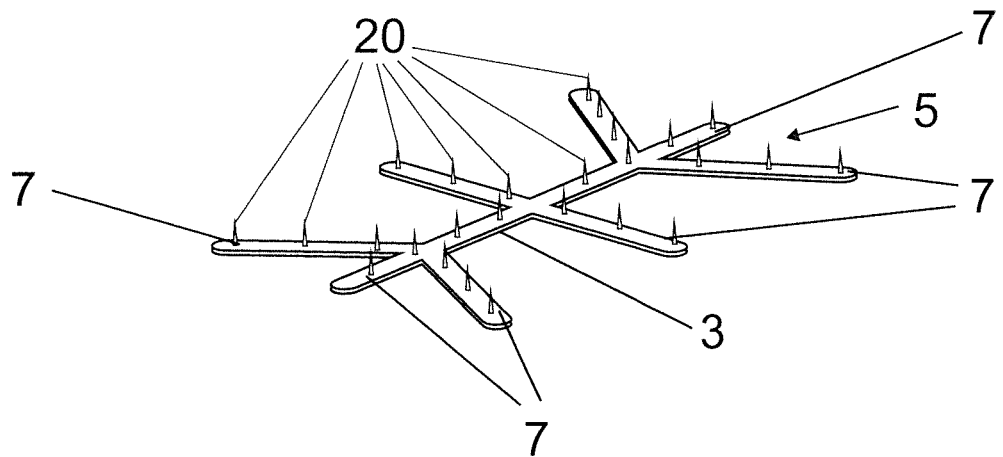
FIG. 9 shows a molding layer with spike-like projections formed thereon as a perspective view.
Figure 10:
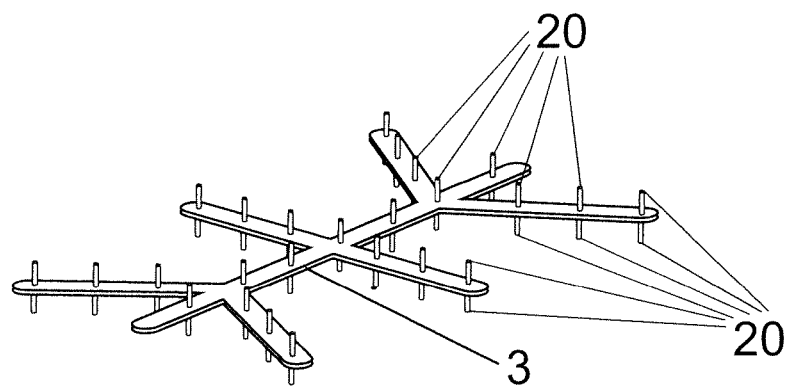
FIG. 10 is a perspective view of a molding layer with pin-shaped projections arranged thereon.

FIG. 9 shows an example of a molding layer 3 with projections 20 formed thereon, and FIG. 10 shows a further example of a molding layer 3. In this example, pin-shaped projections 20 are disposed both at the top side and also at the underside of the molding layer 3.

Figure 11:
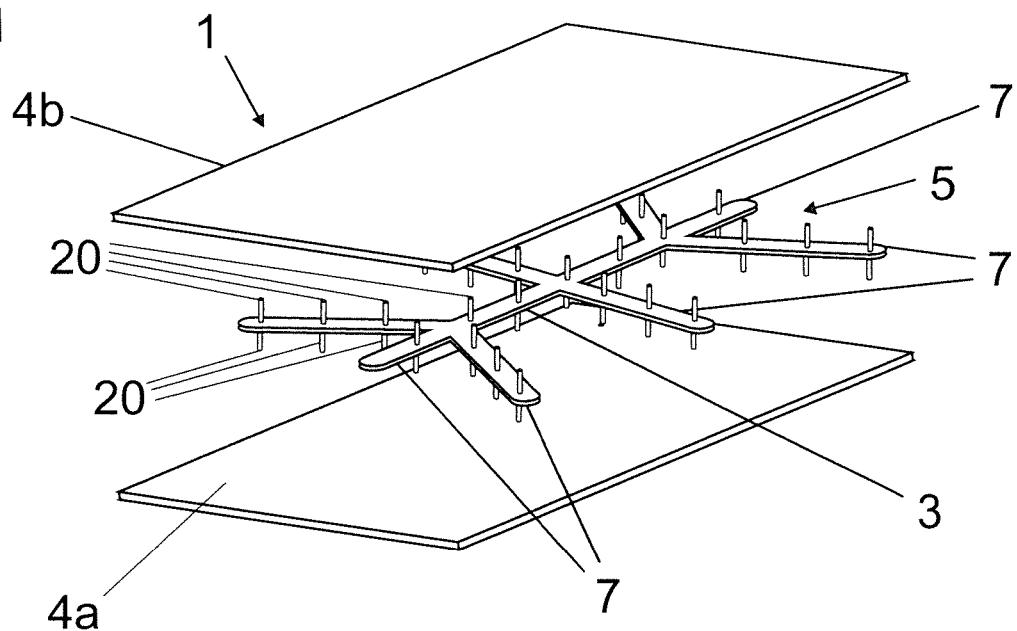
FIG. 11 is an exploded perspective view of an embodiment of the proposed multilayer film.

FIG. 11 shows an exploded perspective view of a proposed multilayer film 1 which includes a molding layer 3 as shown in FIG. 10 and two cover layers 4a and 4b.

Figure 12:
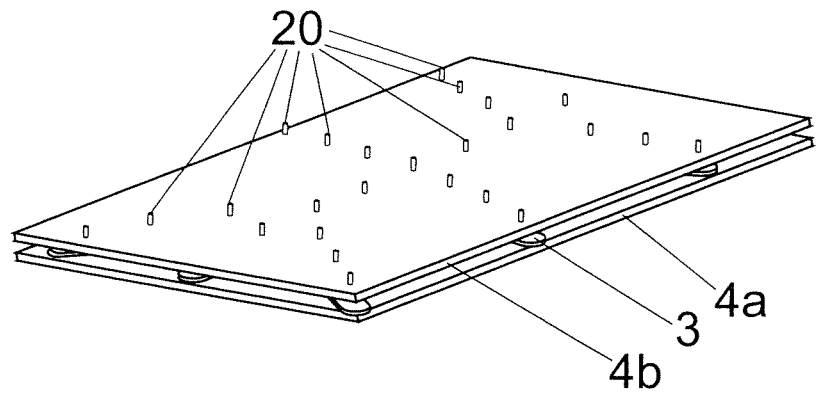
FIG. 12 shows the film of FIG. 11 after application of the cover layers to the molding layer.

FIG. 12 shows the film 1 of FIG. 11 after application of the cover layers 4a and 4b to the molding layer 3. It will be seen that the projections 20 of the molding layer 3 protrude through the cover layers 4a and 4b.

Figure 13:
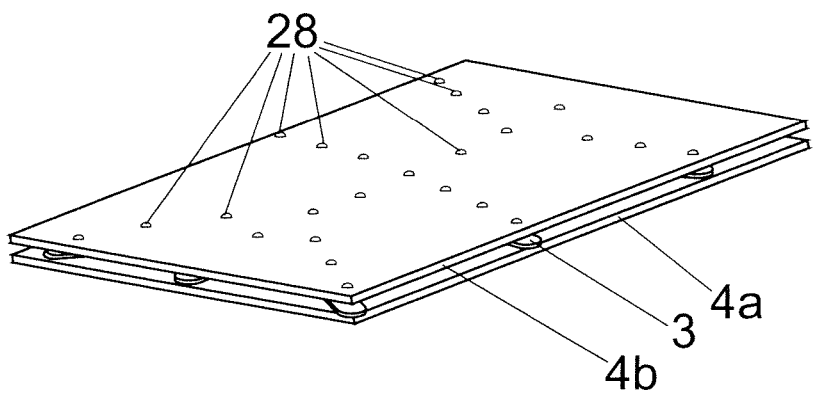
FIG. 13 shows the film of FIG. 12 after pressing of the cover layers to the molding layer.

FIG. 13 shows the film 1 of FIG. 12 after pressing of the cover layers 4a and 4b to the molding layer 3. A fixedly bonded multilayer film 1 was produced by the pressing operation which can be effected mechanically and/or thermally. The projections 20 on the molding layer 3, that project beyond the cover layers 4a, 4b, were deformed by the pressing operation so that rivet-shaped heads 28 were formed, which permit a positively locking connection between the molding layer 3 and the cover layers 4a, 4b.

Figure 14:
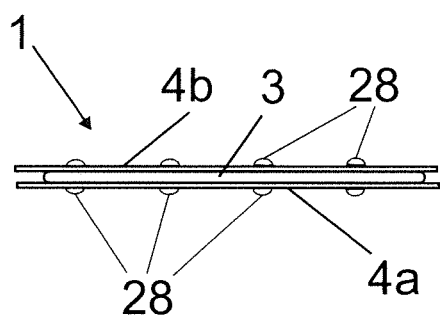
FIG. 14 is a side view of the finished film of FIG. 13.

FIG. 14 shows a side view of the film 1 produced, as shown in FIG. 13.

Figure 15:
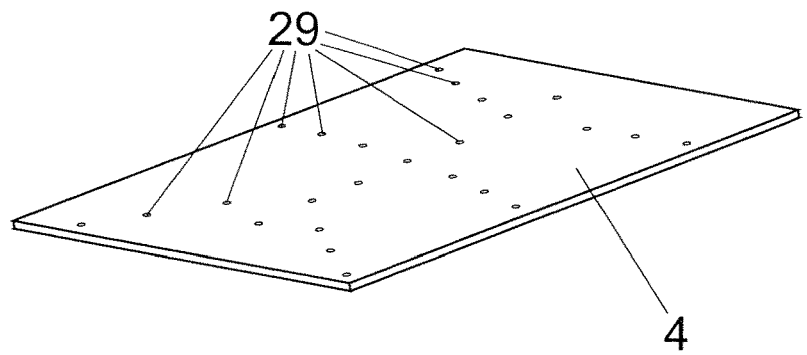
FIG. 15 shows a cover layer with openings for projections on the molding layer.

FIG. 15 shows a cover layer 4 suitable in particular for connection to a molding layer 3 as shown in FIG. 9. That cover layer 4 has openings 29 in the form of holes which correspond to the projections 20 on the molding layer 3 so as to permit the cover layer 4 to be applied to the molding layer 3 in an accurately fitting relationship.

Figure 16:
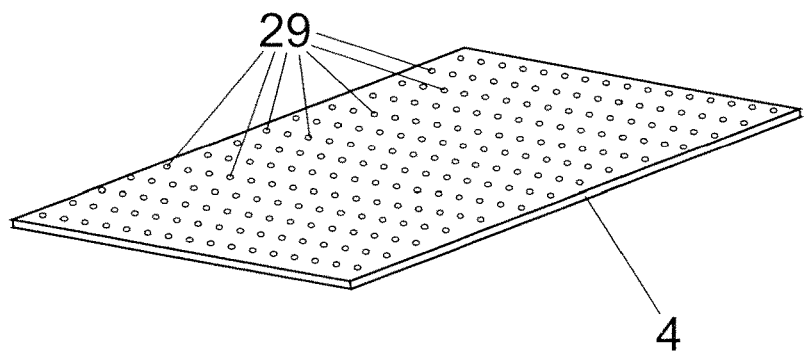
FIG. 16 shows a further cover layer with openings for projections on the molding layer.

FIG. 16 shows a further example of a cover layer 4 which in this case is provided over its full surface area with corresponding openings 29 so that this cover layer 4 can be fitted as desired on to projections 20 on the molding layer 3.

Figure 17:
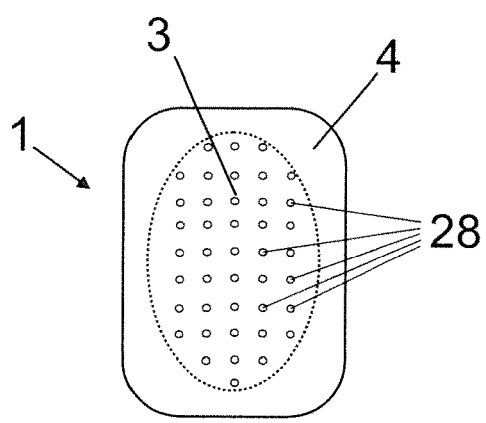
FIG. 17 is a plan view of a further embodiment of the proposed multilayer film.

FIG. 17 shows a plan view of a further example of a proposed film 1. In this example, the cover layer 4 is provided with a pattern of openings 29, through which projections 20 of a molding layer 3—in this example concealed by the cover layer 4—protruded, the ends of the projections 20 being deformed to form heads 28 when the cover layer 4 is thermally and/or mechanically connected to the molding layer 3.

Figure 18:
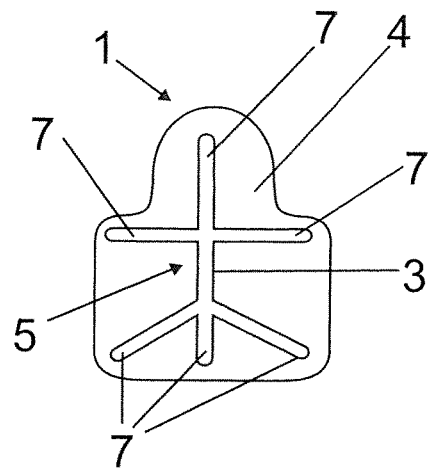
FIGS. 18-21 are plan views of various further embodiments of the proposed multilayer film.
Figure 19:
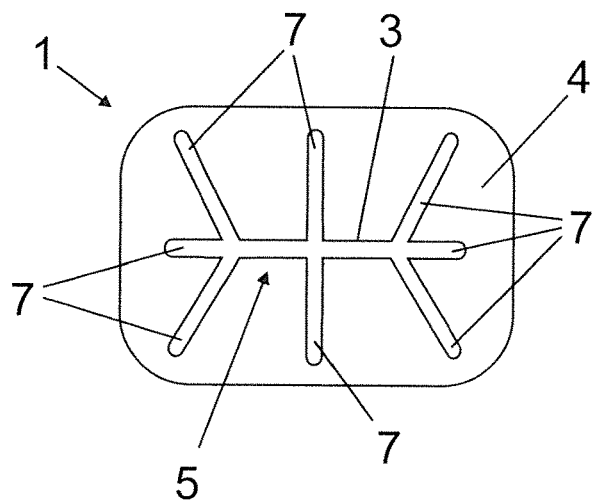

FIGS. 18 and 19 show two further embodiments of a proposed double-layer film 1 with different outside contours in respect of the cover layer 4 and differently formed shaping structures 5 of the molding layer 3.

Figure 20:
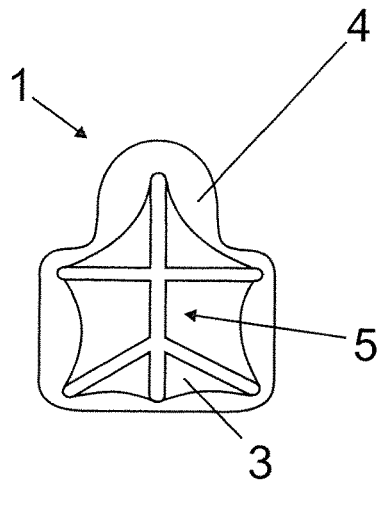
Figure 21:
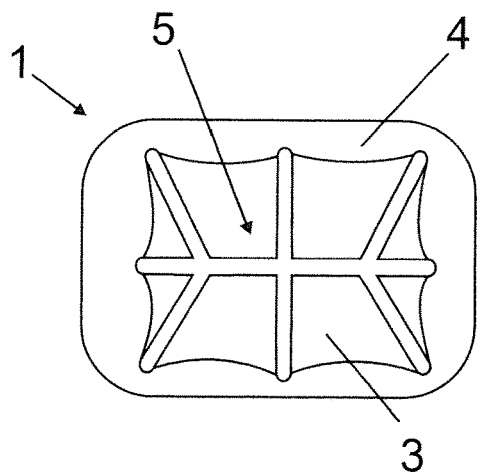

FIGS. 20 and 21 show further examples of proposed films 1. In the examples shown here, the molding layer 3 was respectively applied as a gel to the cover layer 4 and subsequently hardened. The molding layers 3 shown here each includes a shaping structure 5 which was achieved for example by more gel being applied in the regions of the shaping structure 5 so that the molding layers 3 are of differing layer thicknesses. In the region of a shaping structure 5, a molding layer 3 has a respectively greater thickness than in the other regions of the molding layer 3.

FIGS. 22 through 29 each show exploded perspective views of further embodiments of the proposed film 1. The side 9 of a film 1, which in the Figures respectively faces downwardly, is in this case the side 9 of the film 1 that is to face towards a bone defect site 2.

Figure 22:
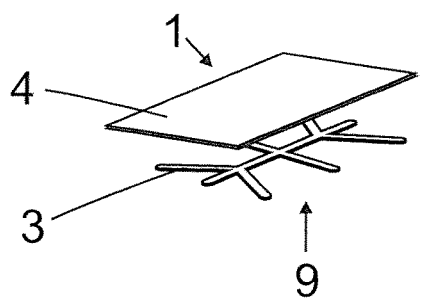
FIGS. 22-29 are exploded perspective views of a number of embodiments of the proposed multilayer film.
Figure 23:
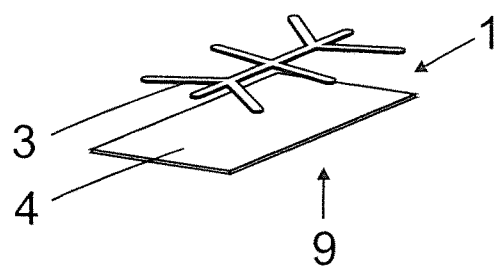
Figure 24:
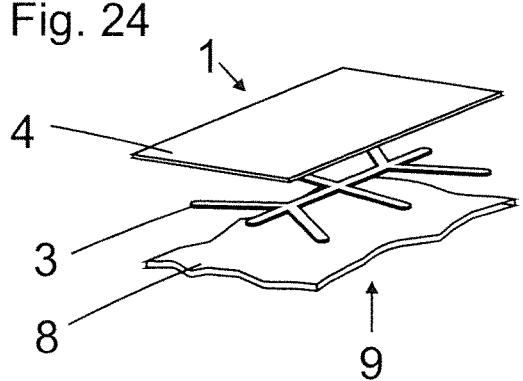
Figure 25:
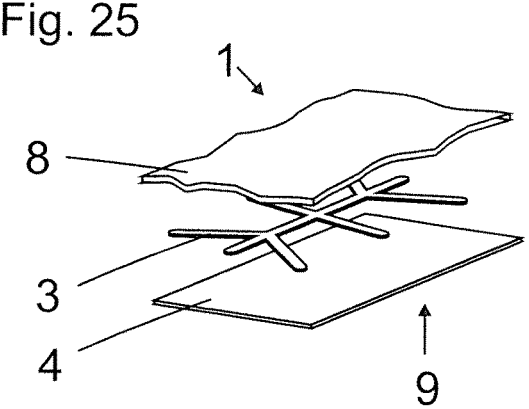
Figure 26:
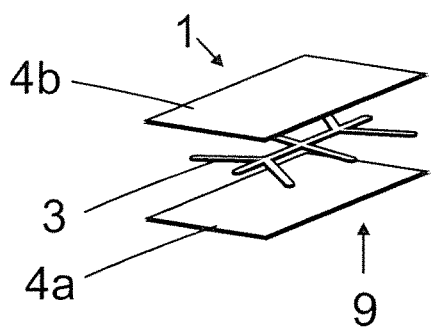
Figure 27:
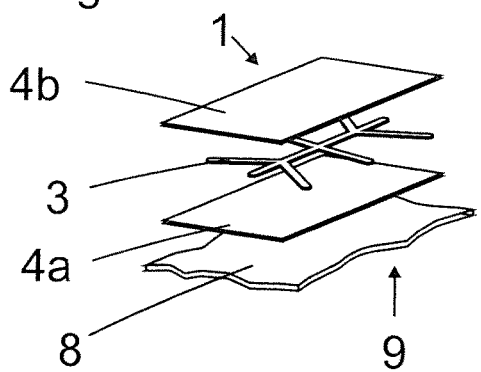
Figure 28:
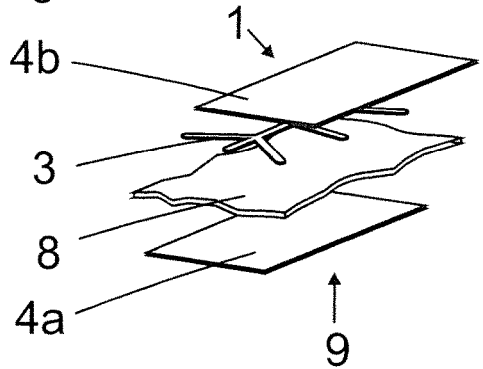
Figure 29:
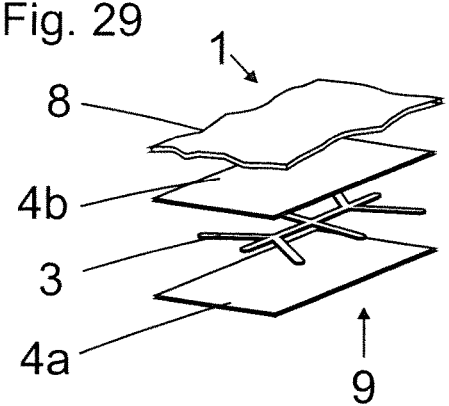

The examples in FIGS. 22 and 23 have a double-layer structure and each include a molding layer 3 and a cover layer 4, wherein the molding layer 3 occupies a smaller surface area than the cover layer 4. The examples in FIGS. 24 and 25 have a triple-layer structure and, besides a molding layer 3 and a cover layer 4, respectively include a carrier layer 8 on which substances such as drugs, growth factors and other substances for promoting and protecting healing and bone formation can be applied.

The examples in FIGS. 26 through 29 each have a molding layer 3 and two cover layers 4a and 4b, wherein the molding layer 3 has a smaller surface area than the cover layers 4a and 4b. The examples in FIGS. 27 through 29 each additionally have a carrier layer 8 which can be equipped with corresponding substances (as described hereinbefore in relation to FIGS. 24 and 25).

Figure 30:
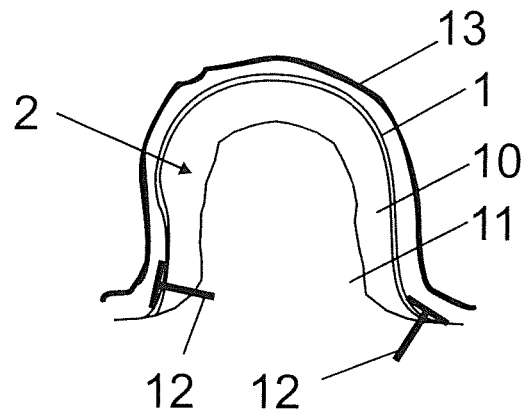
FIG. 30 shows a proposed multilayer film arranged at a bone defect site of a jawbone.

FIG. 30 shows a sectional view of a jawbone 11 with a bone defect site 2. To permit bone construction at the bone defect site 2, a proposed multi-layer film 1 is suitably shaped over the bone defect site 2 and anchored to the jawbone 11 by suitable fixing devices 12. The fixing devices 12 can be, for example, bioresorbable nails. The cavity 10 which is formed between the film 1 and the bone defect site 2 or jawbone 11 can contain bone substitute materials and/or carriers for drugs, growth factors and/or other substances for promoting and protecting healing and bone formation and the provision of a periodontal apparatus around natural teeth to promote bone regeneration. After fitment of the film 1, the gum 13 which has been previously removed or folded back is covered over the film 1 again and suitably sutured. By virtue of the bioresorbability of the film 1 and the fixing devices 12, there is no need for any further operation for removing the film 1 and/or the fixing devices 12 again after bone regeneration has occurred.

Figure 31:
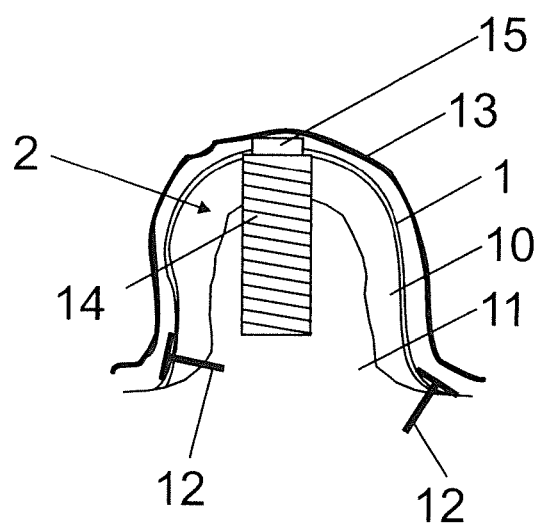
FIG. 31 shows a proposed multilayer film arranged at a bone defect site of a jawbone with implant.

FIG. 31 shows a bone defect site 2 similar to that of FIG. 30, which is covered with a proposed film 1. In this example, an implant 14 has been fitted into the jawbone 11 which is still present, the free end of the implant 14 being provided with a screw 15. For easier accessibility to the implant 14 or the screw 15 thereof it can be provided in this case that the film 1 is already provided with a hole which has been previously stamped out and through which the screw 15 can project.

Figure 32:
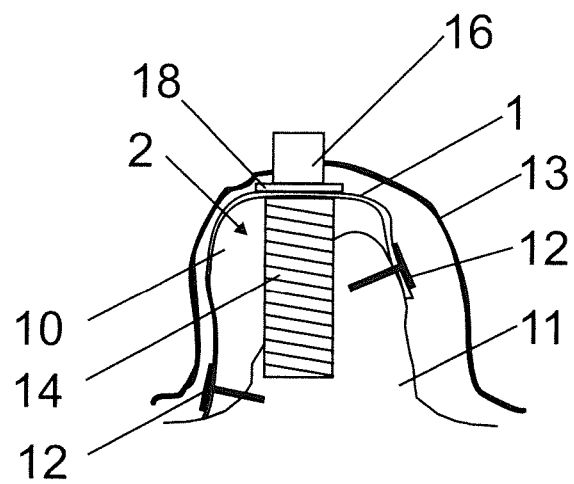
FIG. 32 shows a proposed multilayer film arranged at a bone defect site of a jawbone with implant, support disk and post.

FIG. 32 shows a further example of a bone defect site 2 covered with a proposed film 1. An implant 14 is already fitted in the jawbone 11, a post 16 being arranged at the free end of the implant. The post 16 projects both through the film 1 and also through the gum 13 to facilitate further tooth construction. A support disk 18 is additionally disposed between the post 16 and the film 1. The support disk 18 can provide for closure or sealing-off of the film 1 in that region of the film 1, through which the post 16 projects through the film 1 (penetration region). That is important on the one hand to seal off the film 1 with respect to the oral cavity and thus to prevent the occurrence of inflammation. On the other hand, it is also possible to provide therewith that the film 1 is resorbed more slowly in precisely that sensitive penetration region and can thus better protect that region. The support disk 18 can in this case comprise titanium and project radially beyond the implant 14. The shape of the support disk 18 can be for example round or oval. The support disk 18 can also be so adapted that it can be cut to shape in order to be able to provide for optimum closure of the penetration region by the film 1 or to stabilize the sensitive defective region around the implant 14, depending on the respective situation of use. In this case, the support disk 18 can also be produced in such a way that the film 1 can be clamped and pressed as required in a groove in the support disk 18 to achieve stabilization.

Figure 33:
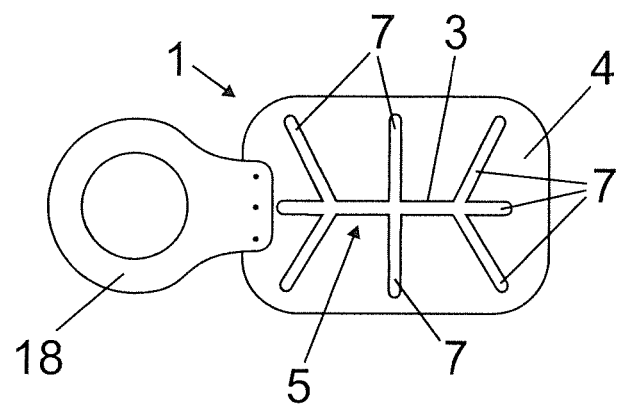
FIG. 33 shows a proposed multilayer film clamped in a groove in a support disk.
Figure 34:
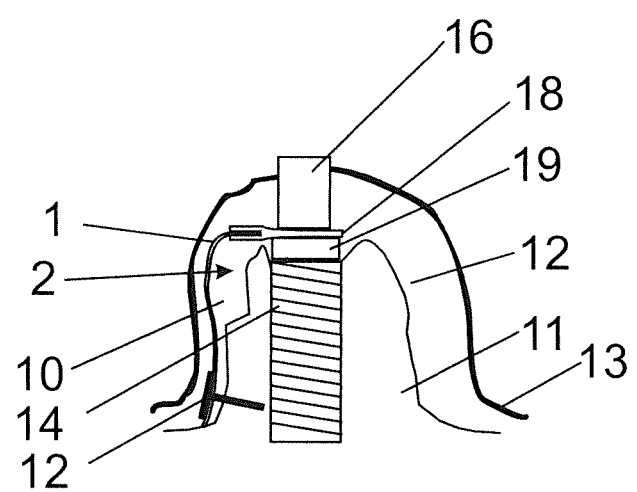
FIG. 34 shows a proposed multilayer film clamped in a groove in a support disk and arranged at a bone defect site of a jawbone with implant and post.

FIG. 33 shows a film 1 which is subsequently clamped and pressed in a groove in a support disk 18, while FIG. 34 shows the arrangement of that film 1 at a bone defect site 2. In the illustrated example, the upper end of the implant 14 (implant head) does not project beyond the jawbone 11 but is disposed beneath the level of the jaw. Depending on how deep the upper end of the implant 14 is disposed in the jawbone 11 or how great the difference in level is between the implant head and the bone level, it is possible to achieve a compensation effect by using inserts 19 of differing heights so that the film 1 or support disk 18 can be fixed without crater formation.

Figure 35:
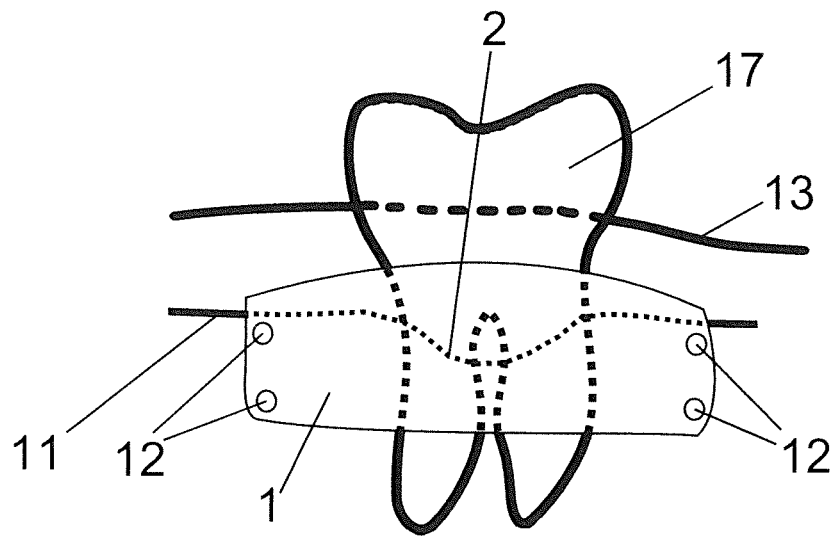
FIG. 35 shows a proposed multilayer film arranged at a bone defect site around a natural tooth.

FIG. 35 shows an example of a bone defect site 2 around a natural tooth 17, covered with a proposed film 1. This example involves the use of the proposed film 1 for covering a periodontal bone defect site 2. The portions of the jawbone 11 and the tooth 17 that are covered by the film 1 are shown in broken line.

Figure 36:
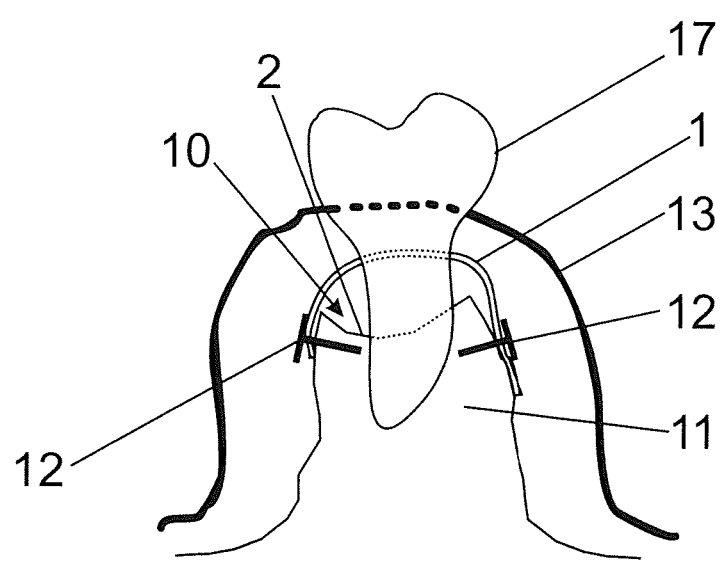
FIG. 36 is a sectional view of a proposed multilayer film arranged at a bone defect site around a natural tooth.

FIG. 36 shows a sectional view of a jawbone 11 with a bone defect site 2 around a natural tooth 17. To permit bone construction and/or production of the periodontal apparatus at the bone defect site 2, a proposed pre-bonded multilayer film 1 is suitably shaped over the bone defect site 2 and the tooth 17 and anchored to the jawbone 11 by suitable fixing devices 12. The fixing devices 12 can be, for example, bioresorbable nails. The cavity 10 which is formed between the film 1 and the bone defect site 2 or jawbone 11 can contain bone substitute materials and/or carriers for drugs, growth factors and/or other substances for promoting and protecting healing and bone formation and production of a periodontal apparatus around natural teeth in order to promote bone regeneration.

After fitment of the film 1, the gum 13 which has been previously removed or folded back is covered over the film 1 again and suitably sutured. By virtue of the bioresorbability of the film 1 and the fixing devices 12, there is no need for a further operation to remove the film 1 and/or the fixing devices 12 again after bone regeneration has taken place.

The invention claimed is:

1. A method of producing a multilayer film for covering a bone defect site, said method comprising:
    applying a bioresorbable and non-mesh cover layer to a thermally deformable and bioresorbable molding layer to form a non-mesh multilayer film, the cover layer being thermally and/or mechanically connected to the molding layer,
    wherein the molding layer comprises a bioresorbable polymer material and a shaping structure configured to allow the non-mesh multilayer film to be shaped to the bone defect site, the shaping structure having at least one of a grid shape and a strut-shaped shaping molding element;
    wherein the cover layer comprises a bioresorbable collagen material such that the molding layer is stiffer than the cover layer, the cover layer being configured to cover the bone defect site;
    wherein the cover layer and the molding layer are connected to each other during said applying by (i) pressing spike-shaped projections on the molding layer into the cover layer such that tips of the projections protrude through the cover layer, the projections being formed to have a one-piece construction with the molding layer, and (ii) deforming the tips of the projections protruding through the cover layer to obtain a positively-locked connection between the molding layer and the cover layer.

2. The method as set forth in claim 1, wherein the spike-shaped projections pass entirely through the cover layer when the cover layer is applied to the molding layer.

3. The method as set forth in claim 2, wherein the cover layer and the molding layer are further connected to each other during said applying by rivets or pins passing through the molding layer and the cover layer.

4. The method as set forth in claim 1, wherein the cover layer and the molding layer are further connected to each other during said applying by rivets or pins passing through the molding layer and the cover layer.

5. The method as set forth in claim 1, wherein said applying comprises heating the molding layer to thermally connect the cover layer to the molding layer.

6. The method as set forth in claim 5, wherein the molding layer is heated to a temperature in a region of between 50° C. and 70° C.

7. The method as set forth in claim 6, wherein the molding layer is heated to a temperature of 60° C.

8. The method as set forth in claim 1, wherein the cover layer is pressed to the molding layer during said applying.

9. The method as set forth in claim 8 wherein, during said pressing, a surface of a pressing apparatus facing at least one of the molding layer and the cover layer is heated.

10. The method as set forth in claim 9, wherein the surface of the pressing apparatus is heated to a temperature in a region of between 50° C. and 70° C.

11. The method as set forth in claim 10, wherein the surface of the pressing apparatus is heated to a temperature of 60° C.

12. The method as set forth in claim 1, further comprising applying an adhesive to the multilayer film for securing the pre-bonded multilayer film to a gum surrounding the bone defect site.

13. The method as set forth in claim 12, wherein the bone defect site is around a tooth.

14. A multilayer film for covering a bone defect site, said multilayer film comprising:
    a thermally deformable bioresorbable molding layer comprising a bioresorbable polymer material and a shaping structure configured to allow the multilayer film to be shaped to the bone defect site, the shaping structure having at least one of a grid shape and a strut-shaped shaping molding element;
    a bioresorbable non-mesh cover layer thermally and/or mechanically connected to the thermally deformable and bioresorbable molding layer to form a non-mesh multilayer film, the cover layer comprising a bioresorbable collagen material such that the molding layer is stiffer than the cover layer, the cover layer being configured to cover the bone defect site;
    connecting elements for connecting the cover layer to the molding layer, the connecting elements including spike-shaped projections on the molding layer pressed into the cover layer such that tips of the projections protrude through the cover layer, the projections having a one-piece construction with the molding layer, the tips of the projections protruding through the cover layer being deformed to obtain a positively-locked connection between the molding layer and the cover layer.

15. The multilayer film as set forth in claim 14, further comprising rivets or pins passing through the molding layer and the cover layer to connect the cover layer and the molding layer.

16. The multilayer film as set forth in claim 14, wherein the bioresorbable collagen material includes type-I-collagen and/or type-III-collagen.

17. The multilayer film as set forth in claim 14, wherein the bioresorbable polymer material includes lactic acid.

18. The multilayer film as set forth in claim 17, wherein the lactic acid is L-lactic acid or derivatives thereof.

19. The multilayer film as set forth in claim 17, wherein the proportion of lactic acid in the bioresorbable polymer material is at least 70%.

20. The multilayer film as set forth in claim 19, wherein the proportion of lactic acid in the bioresorbable polymer material is between 80% and 95%.

21. The multilayer film as set forth in claim 14, wherein the bioresorbable polymer material includes glycolic acid.

22. The multilayer film as set forth in claim 21, wherein the proportion of glycolic acid in the bioresorbable polymer material is no more than 30%.

23. The multilayer film as set forth in claim 22, wherein the proportion of glycolic acid in the bioresorbable polymer material is between 15% and 20%.

24. The multilayer film as set forth in claim 14, wherein the molding layer and the cover layer have different surface areas.

25. The multilayer film as set forth in claim 24, wherein the molding layer has a smaller surface area than the cover layer.

26. The multilayer film as set forth in claim 14, wherein at least one of the molding layer and the cover layer is planar throughout.

27. The multilayer film as set forth in claim 14, wherein the shaping structure has at least a portion having at least one of:
    a convexly curved edge,
    a concavely curved edge,
    a convexly curved shape, and/or
    a concavely curved shape.

28. The multilayer film as set forth in claim 14, wherein the shaping structure has a strut-shaped shaping molding element.

29. The multilayer film as set forth in claim 14, wherein the shaping structure is grid-shaped.

30. The multilayer film as set forth in claim 14, wherein at least a portion of the shaping structure has a thickness greater than a thickness of a remainder of the molding layer to reinforce the molding layer.

31. The multilayer film as set forth in claim 14, further comprising a carrier layer for carrying thereon drugs, growth factors, or other substances for promoting and protecting healing and bone formation.

32. The multilayer film as set forth in claim 14, further comprising an adhesive on the multilayer film for securing the pre-bonded multilayer film to a gum surrounding the bone defect site.

33. The multilayer film as set forth in claim 32, wherein the bone defect site is around a tooth.

* * * * *